(12) United States Patent
Studer et al.

(10) Patent No.: US 8,156,782 B2
(45) Date of Patent: Apr. 17, 2012

(54) TEST ADAPTER FOR A GAS-MEASURING DEVICE

(75) Inventors: Matthias Studer, Krummesse (DE); Mladen Schlichte, Lübeck (DE); Markus Wansing, Lübeck (DE); Volker Kuhn, Stockelsdorf (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 588 days.

(21) Appl. No.: 12/181,610

(22) Filed: Jul. 29, 2008

(65) Prior Publication Data

US 2009/0071226 A1 Mar. 19, 2009

(30) Foreign Application Priority Data

Sep. 15, 2007 (DE) .......................... 10 2007 044 179

(51) Int. Cl.
*G01N 27/26* (2006.01)

(52) U.S. Cl. .................... 73/1.06; 73/864.83; 73/864.84; 73/864.85

(58) Field of Classification Search ............... 73/866.84, 73/866.85
See application file for complete search history.

(56) References Cited

U.S. PATENT DOCUMENTS

| | | | |
|---|---|---|---|
| 4,700,560 A | 10/1987 | Hoffa et al. | |
| 5,051,240 A * | 9/1991 | Nakai et al. | 422/83 |
| 5,753,508 A * | 5/1998 | Robertson et al. | 436/2 |
| 6,701,773 B2 | 3/2004 | Rabenecker | |
| 6,902,701 B1 * | 6/2005 | Hughes et al. | 422/83 |
| 2006/0016346 A1 * | 1/2006 | Mulle et al. | 99/279 |

FOREIGN PATENT DOCUMENTS

| | | |
|---|---|---|
| DE | 32 13 241 A1 | 10/1983 |
| DE | 102 31 515 C1 | 7/2003 |
| JP | 57-128 840 | 8/1982 |

* cited by examiner

*Primary Examiner* — Hezron E Williams
*Assistant Examiner* — Paul West
(74) *Attorney, Agent, or Firm* — McGlew and Tuttle, P.C.

(57) ABSTRACT

A test adapter for the saturated vapor calibration of gas-measuring devices. The test adapter (2) has, in an adapter housing (15), a peripheral edge (7) for receiving a gas-measuring device and has a depression (10) for receiving the sample liquid in the area of the gas-sensitive surface of the gas-measuring device.

20 Claims, 4 Drawing Sheets

TEST ADAPTER FOR A GAS-MEASURING DEVICE

CROSS REFERENCE TO RELATED APPLICATIONS

This application claims the benefit of priority under 35 U.S.C. §119 of German Patent Application 10 2007 044 179.9 filed 15 Sep. 2007, the entire contents of which are incorporated herein by reference.

FIELD OF THE INVENTION

The present invention relates to a test adapter for a gas-measuring device.

BACKGROUND OF THE INVENTION

A measuring device for gas analysis, in which test gas is admitted to the gas sensor of a measuring head by means of a measured gas pump, is known from DE 102 31 515 C1, which corresponds to U.S. Pat. No. 6,701,773 which is incorporated by reference. A plug-in adapter, which has individual gas ducts, via which measured gas is drawn in by means of the measured gas pump and is delivered to the gas-specific surface of the gas sensor, is connected to the measuring head.

The prior-art gas-measuring device is also suitable for detecting volatile substances, which are adsorbed by the pump diaphragm of the measuring gas pump. The plug-in adapter is attached for this to the measuring head such that the gas sensor is located in front of the measured gas pump and is directly exposed to the volatile substance.

The prior-art gas-measuring device is suitable for continuous gas sampling, during which measured gas is drawn from a gas source.

A function test can be carried out with the prior-art gas-measuring device only by connecting it to a test gas source. Carrying along test gas sources makes handling difficult, especially because a simple function test, to be performed to determine whether or not a gas-measuring device responds to a certain gas, is sufficient in many cases.

Multi-gas-measuring devices, with which different components in a gas sample can be detected simultaneously, are known. Such multi-gas-measuring devices contain different measuring systems, in which infrared optical, electrochemical or catalytic detection methods are used. Multi-gas-measuring devices are often also designed as compact, portable measuring devices, which can simply be carried along and perform the gas concentration measurement directly at a possible hazard site.

The calibration of such gas-measuring devices for combustible materials with high-boiling hydrocarbons such as nonane and xylene is very complicated and cumbersome according to the current state of the art. Nonane is used as an additive in motor fuels, is readily combustible and has a gasoline-like odor. It is known to use, e.g., a calibration chamber for this, in which a certain quantity of liquid is dispensed into a known chamber volume by means of a plunger syringe and evaporated. The device to be calibrated is connected to the chamber. At the same time, a fan present in the chamber must be started in order to swirl the vapor. Handling requires utmost care because possible leaks in the chamber or errors in dispensing the liquid may lead to incorrect calibration. The high-boiling hydrocarbons evaporate very slowly at low ambient temperatures and lead to additional errors.

If the so-called saturated vapor calibration is used, relatively large quantities of liquid must be dispensed into the calibrating volume and ventilated there until a maximum vapor pressure becomes established, which depends on the temperature only. This temperature is measured with an additional temperature measuring device, and the concentration is determined from corresponding charts or diagrams.

SUMMARY OF THE INVENTION

An object of the present invention is to provide a device for saturated vapor calibration for gas-measuring devices.

According to the present invention, a test adapter is provided comprising a shell adapted to the geometric, external dimensions of the gas-measuring device with an integrated temperature measurement. The shell has a depression for receiving the sample liquid in the area of the gas-sensitive surface of the gas-measuring device. The upper side of the depression is located directly at the gas-sensitive surface of the gas-measuring device. The liquid level of the sample liquid within the depression is selected to be such that a gas volume in which the saturated vapor concentration of the sample liquid becomes established is present between the gas-sensitive surface and the sample liquid.

A stepped filling level indicator, whose lower step indicates the minimum filling level and whose upper step indicates the maximum filling level, is advantageously provided within the depression. The sample liquid can be filled into the depression by means of a syringe. The temperature indicator is advantageously designed in the form of a temperature measuring strip, which is arranged within the test adapter on the surface facing the gas-measuring device. Thus, the temperature-measuring strip is located in the immediate vicinity of the depression provided with the sample liquid.

The test adapter has an edge, which extends peripherally at least partially and into which the gas-measuring device is inserted. The peripheral edge is adapted to the outer contour of the housing of the gas-measuring device, so that the gas-sensitive surface of the gas-measuring device is located exactly above the depression of the test adapter and covers the depression from the top.

On its underside, the test adapter has feet, with which it can be placed on a horizontal surface, especially a table.

The adapter housing is shaped to receive the one side of the gas-measuring device having the gas sensitive surface. The depression of the adapter surface being arranged in an area of the gas sensitive surface when the gas-measuring device is received by the adapter housing. The depression and the adapter housing being arranged to hold saturated vapors of the sample liquid in communication with the gas sensitive surface of the gas-measuring device when the gas-measuring device is received by the adapter housing.

In particular, the depression and the adapter housing are shaped to entrap the saturated vapors of the sample liquid between the one side of the gas-measuring device and the side of the adapter housing with the depression, when the gas-measuring device is received by the adapter housing.

The function of the gas-measuring device is checked such that the test adapter is first placed on a horizontal surface and the depression is filled with sample liquid. The liquid level of the sample liquid is set within the depression such that it is between the minimum mark and maximum mark. The gas-measuring device is then placed onto the test adapter such that the gas-sensitive surface lies above the depression. The inner contour of the test adapter and the edge extending peripherally on the outside are designed such that the gas-measuring device can be connected to the test adapter in a preferred position only. The function test is carried out automatically by the gas-measuring device after the saturated vapor atmosphere of the sample liquid has acted on the gas-sensitive surface of the gas-measuring device for a certain time. After conclusion of the function test, the gas-measuring device sends a signal tone, which signals the end of the testing and calibration phase.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
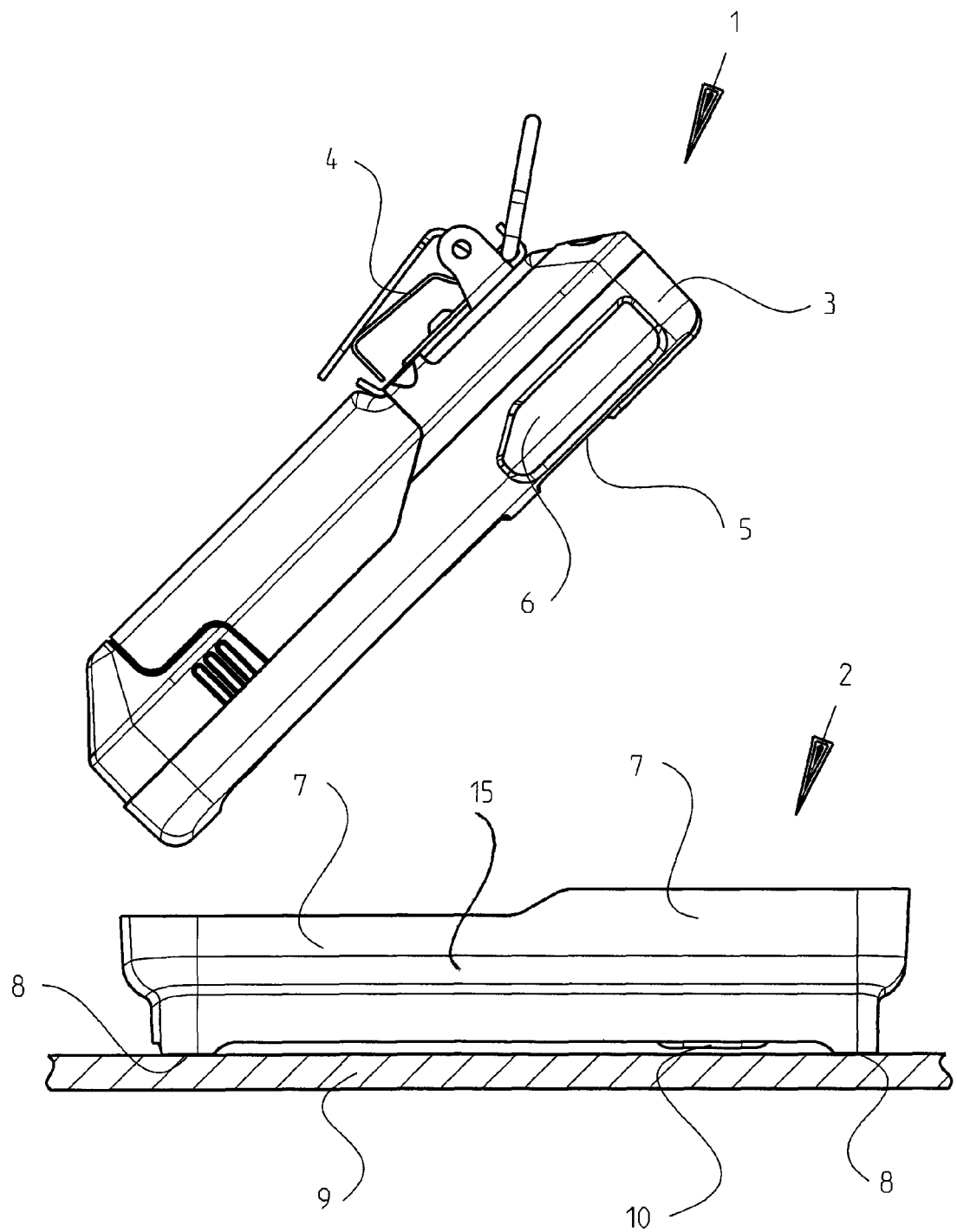
FIG. 1 is a side view of a gas-measuring device and of a test adapter.

Referring to the drawings in particular, FIG. 1 shows a portable gas-measuring device 1 and a test adapter 2. The components of the gas-measuring device 1 are accommodated in a housing 3. A fastening clamp 4, with which the gas-measuring device 1 can be fastened to the work clothing of a person, not shown more specifically, is located on the rear side, and a gas-sensitive surface 5, which is exposed to the atmosphere, is located on the front side. A catalytic gas sensor 6 is arranged behind the gas-sensitive surface 5 for detecting high-boiling hydrocarbons such as nonane or xylene.

On its upper side, the test adapter 2 has a peripheral edge 7, which has a design corresponding to the outer contour of the housing 3. The test adapter 2 has feet 8 on its underside, with which the test adapter 2 can be placed on a horizontal surface 9. The test adapter has a depression 10 for receiving a sample liquid in the area of the gas-sensitive surface 5 of the gas-measuring device 1.

Figure 2:
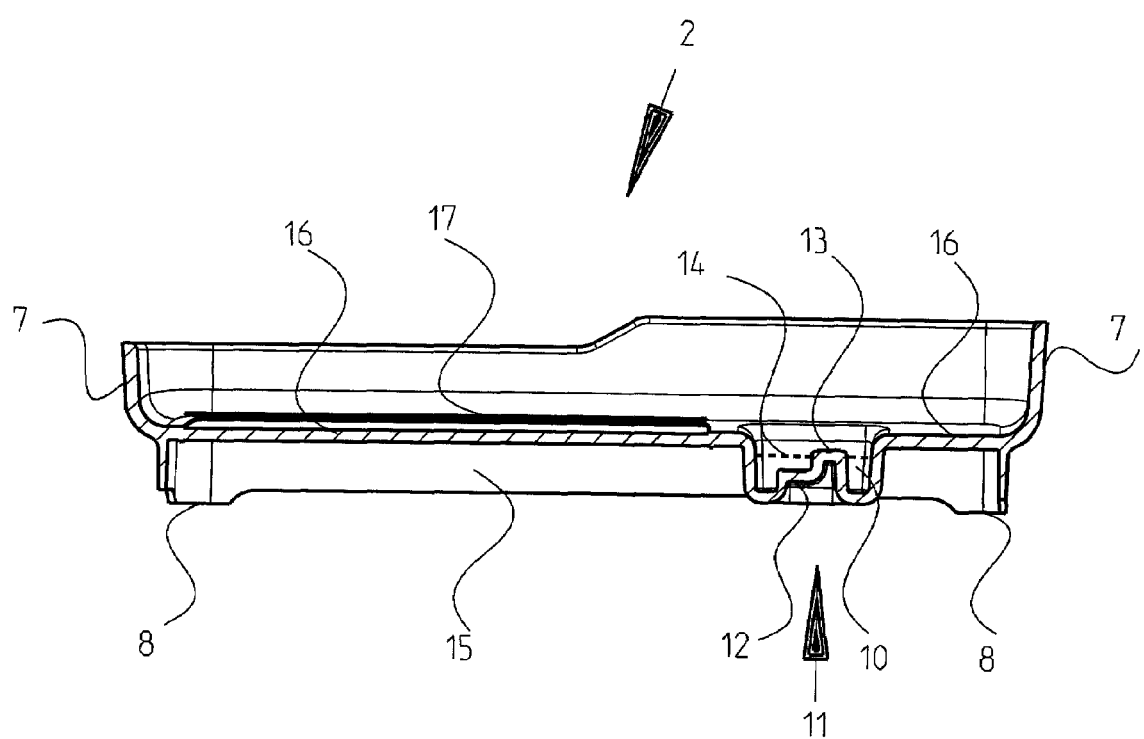
FIG. 2 is a longitudinal sectional view of the test adapter according to FIG. 1.

FIG. 2 shows the longitudinal section of the test adapter 2 according to FIG. 1. Identical components are designated by the same reference numbers as in FIG. 1. A liquid level indicator 11, which has a lower, minimum mark 12 and an upper, maximum mark 13, is provided within the depression 10. The sample liquid, nonane or xylene, is filled into the depression 10 such that the liquid level 14 is located between the minimum mark 12 and the maximum mark 13. The adapter housing 15 of the test adapter 2 is designed such that it has a support surface 16 for the gas-measuring device 1. A temperature strip 17, with which the temperature of the adapter housing 15 and hence the temperature of the sample liquid filled into the depression 10 is detected, is attached to the support surface 16. Since the volume of the sample liquid is small compared to the heat capacity of the adapter housing 15, rapid temperature equalization will take place between the adapter housing 15 and the sample liquid.

Figure 3:
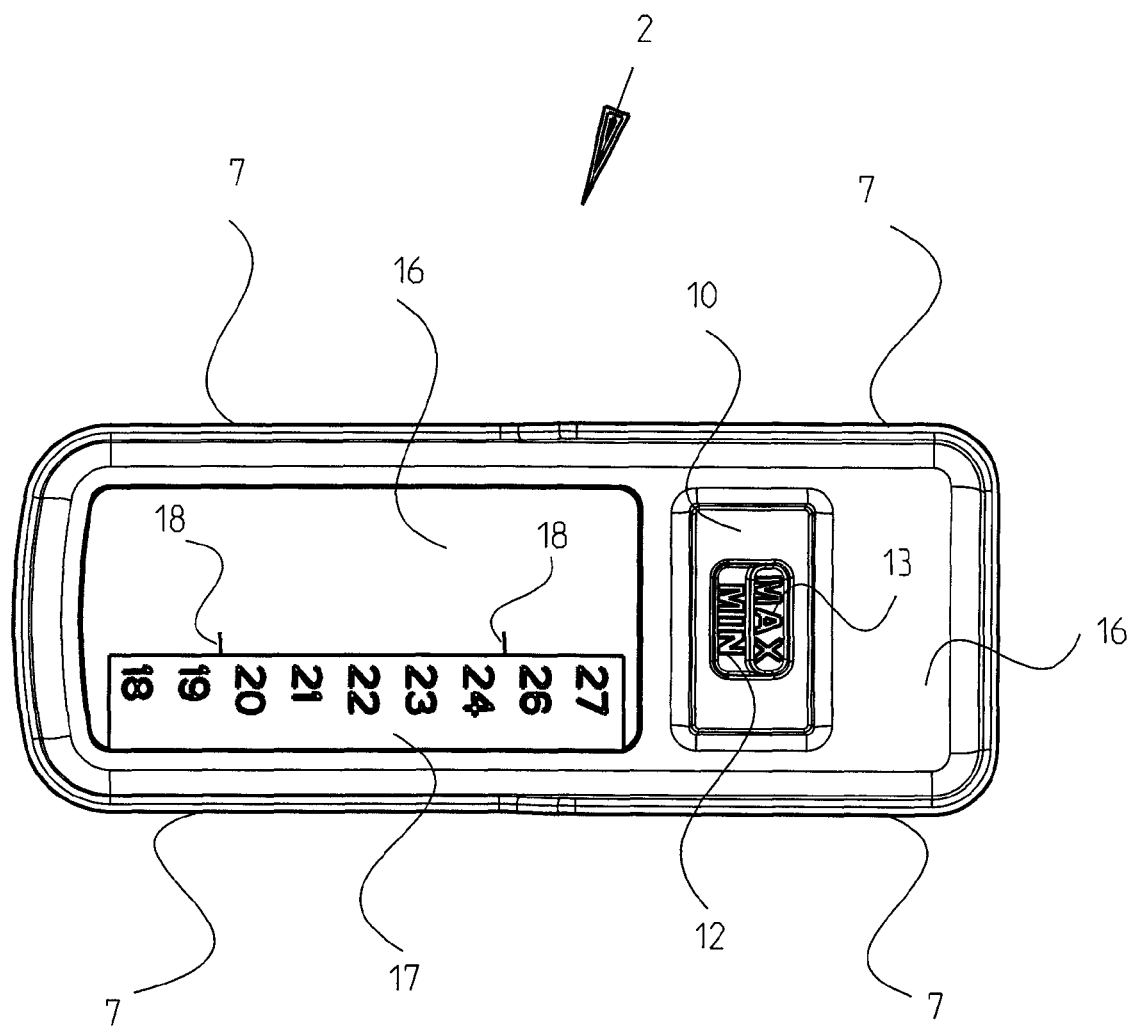
FIG. 3 is a top view of the test adapter.

FIG. 3 shows a top view of the test adapter according to FIG. 1. Temperature marks 18, which indicate a permissible temperature range for testing the function of the gas-measuring device 1, are arranged on the temperature-measuring strip 17. If the measured temperature is outside the range indicated by the temperature marks 18, the function test must not be performed.

Figure 4:
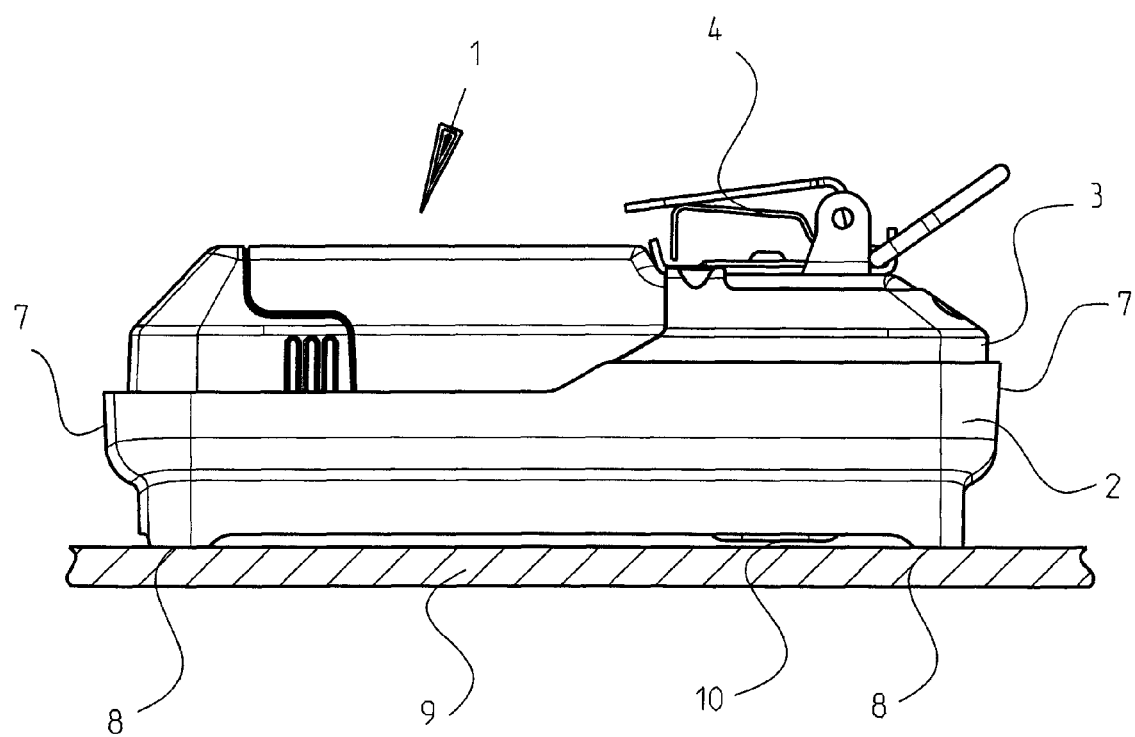
FIG. 4 is a side view of a test adapter with the gas-measuring device attached.

FIG. 4 shows the test adapter 2 with the gas-measuring device 1 attached. The housing 3 of the gas-measuring device 1 is surrounded here by the peripheral edge 7 of the test adapter 2.

While specific embodiments of the invention have been shown and described in detail to illustrate the application of the principles of the invention, it will be understood that the invention may be embodied otherwise without departing from such principles.

What is claimed is:

1. A test adapter for a gas-measuring device, the adapter comprising:
    an adapter housing with an edge extending peripherally, and said adapter housing receiving the gas-measuring device in a gas-measuring device calibration state, said adapter housing having an adapter housing surface, at least a portion of said adapter housing surface defining a depression, said depression receiving a sample liquid, said depression being arranged in an area of a gas-sensitive surface of the gas-measuring device when said adapter housing receives the gas-measuring device in said gas-measuring device calibration state, said gas-sensitive surface of said gas-measuring device being arranged at a position above the sample liquid in said gas-measuring device calibration state, said adapter housing being located at a spaced location from the gas-measuring device in a gas-measuring state; and
    a temperature indicator arranged on said adapter housing.

2. A test adapter in accordance with claim 1, wherein said temperature indicator is arranged as a temperature-measuring strip on another portion of said adapter housing surface, said another portion of said adapter housing surface being arranged facing the gas-measuring device when said adapter housing receives the gas-measuring device.

3. A test adapter in accordance with claim 2, further comprising:
    a filling level indicator for the sample liquid arranged in an area of said depression receiving the sample liquid.

4. A test adapter in accordance with claim 3, wherein a stepped portion of said at least said portion of said adapter housing defines said filling level indicator, said stepped portion having a minimum stepped portion and a maximum stepped portion, said minimum stepped portion defining a minimum fluid fill level, said maximum stepped portion defining a maximum fluid fill level.

5. A test adapter in accordance with claim 4, wherein the sample liquid is nonane or xylene.

6. A test adapter in accordance with claim 1, further comprising:
    a filling level indicator for the sample liquid arranged in an area of said depression receiving the sample liquid.

7. A test adapter in accordance with claim 6, wherein a stepped portion of said at least said portion of said adapter housing defines said filling level indicator, said stepped portion having a minimum stepped portion and a maximum stepped portion, said minimum stepped portion defining a minimum fluid fill level, said maximum stepped portion defining a maximum fluid fill level.

8. A test adapter in accordance with claim 1, wherein the sample liquid is nonane or xylene.

9. A test adapter in accordance with claim 1, further comprising:
    the gas-measuring device, said gas-measuring device measuring a gas in said gas-measuring state.

10. A test system, the system comprising:

a gas-measuring device comprising a gas-measuring state and a calibration state, said gas-measuring device measuring a gas in said gas-measuring state;

an adapter housing receiving one side of the gas-measuring device in said calibration state, said gas-measuring device being detached from said adapter housing in said gas-measuring state, the one side of the gas-measuring device having a gas sensitive surface, said adapter housing having a support surface, wherein a portion of said support surface defines a depression, said depression being arranged in an area of the gas sensitive surface with said adapter housing receiving the gas-measuring device in said calibration state, said depression holding a sample liquid, said depression and said adapter housing being arranged to hold saturated vapors of the sample liquid in communication with the gas sensitive surface of the gas-measuring device with said adapter housing receiving the gas-measuring device in said calibration state, said sample liquid being located opposite said gas-sensitive surface in said calibration state; and a temperature indicator mounted on said adapter housing and indicating a temperature of the sample liquid.

11. A test system in accordance with claim 10, wherein said temperature indicator only displays a temperature range valid for calibration of the gas measuring device.

12. A test system in accordance with claim 10, wherein said temperature indicator is arranged as a temperature-measuring strip on another portion of said support surface of said adapter housing, said support surface being arranged facing the gas-measuring device when said adapter housing receives the gas-measuring device.

13. A test system in accordance with claim 10, further comprising:

a filling level indicator for the sample liquid arranged in an area of said depression receiving the sample liquid.

14. A test system in accordance with claim 13, wherein said portion of said support surface has a first stepped portion and a second stepped portion, said first stepped portion and said second stepped portion defining said filling level indicator, said first stepped portion defining a minimum fluid fill level, said second stepped portion defining a maximum fluid fill level.

15. A test system in accordance with claim 10, wherein the gas measuring device measures one of nonane and xylene.

16. A test system in accordance with claim 10, wherein said depression and said adapter housing are shaped to entrap the saturated vapors of the sample liquid between said one side of the gas-measuring device and one side of said adapter housing when the gas-measuring device is received by said adapter housing.

17. A test system, comprising:

a gas-measuring device, said gas-measuring device having a gas sensitive surface extending along one side thereof;

a sample fluid;

an adapter housing receiving said gas-measuring device in a gas-measuring device calibration state, said adapter housing having a support surface, wherein a portion of said support surface defines a depression, said depression being arranged opposite said gas sensitive surface with said adapter housing receiving the gas-measuring device in said gas-measuring device calibration state, said depression receiving said sample liquid, said depression and said adapter housing being arranged to hold saturated vapors of said sample fluid in communication with said gas sensitive surface of said gas-measuring device in said gas-measuring device calibration state, said gas-measuring device measuring a gas at a spaced location from said adapter housing in a gas-measuring state; and a temperature indicator mounted on another portion of said support surface, said temperature indicator indicating a temperature of said sample fluid.

18. A test system in accordance with claim 17, wherein said temperature indicator is arranged as a temperature-measuring strip on another portion of said support surface of said adapter housing, said support surface being arranged facing the gas-measuring device in said gas-measuring device calibration state, said adapter housing having an adapter housing edge surface, said adapter housing edge surface extending peripherally about at least a portion of an outer surface of said gas-measuring device in said gas-measuring device calibration state.

19. A test system in accordance with claim 17, wherein said temperature indicator only displays a temperature range valid for calibration of the gas measuring device.

20. A test system in accordance with claim 17, further comprising:

a filling level indicator for the sample liquid arranged in an area of said depression receiving the sample liquid, said gas-measuring device comprising a gas sensor arranged opposite said gas-sensitive surface, wherein said portion of said support surface has a first stepped portion and a second stepped portion, said first stepped portion and said second stepped portion defining said filling level indicator, said first stepped portion defining a minimum fluid fill level, said second stepped portion defining a maximum fluid fill level.

* * * * *